United States Patent
Palepu et al.

(10) Patent No.: US 6,420,412 B2
(45) Date of Patent: Jul. 16, 2002

(54) EPROSARTAN DIHYDATE AND A PROCESS FOR ITS PRODUCTION AND FORMULATION

(75) Inventors: Nageswara R. Palepu, Northwood (GB); Gopadi M. Venkatesh, King of Prussia, PA (US); Sarma Duddu, Redwood City, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/809,593

(22) Filed: Mar. 15, 2001

Related U.S. Application Data

(63) Continuation of application No. 09/571,464, filed on May 16, 2000, now abandoned, which is a continuation of application No. 09/155,431, filed as application No. PCT/US97/04877 on Mar. 26, 1997, now abandoned.

(60) Provisional application No. 60/014,414, filed on Mar. 29, 1996.

(51) Int. Cl.$^7$ .................. A61K 31/415; C07D 233/02
(52) U.S. Cl. .................................. 514/397; 548/315.1
(58) Field of Search ...................... 548/315.1; 574/397

(56) References Cited

U.S. PATENT DOCUMENTS 5,185,351 A   2/1993   Finkelstein et al.

*Primary Examiner*—Deborah C. Lambkin
(74) *Attorney, Agent, or Firm*—Laura K. Madden; Mary E. McCarthy; Charles M. Kinzig

(57) ABSTRACT

The invention relates to (E)-α-[2-n-butyl-1-[(4-carboxyphenyl)methyl]-1-H-imidazol-5-yl]methylene-2-thiopheneproprionic acid monomethanesulfonate dihydrate, a process for its production, compositions containing the compound and methods of using the compound to block angiotensin II receptors and to treat hypertension, congestive heart failure and renal failure.

41 Claims, 3 Drawing Sheets

EPROSARTAN DIHYDATE AND A PROCESS FOR ITS PRODUCTION AND FORMULATION

This application is a continuation of U.S. Ser. No. 09/571,464, filed May 12, 2000 now abandoned, which is a continuation of U.S. Ser. No. 09/155,431, filed on Sep. 28, 1998, now abandoned, which is a 371 of PCT/US97/04877, filed on Mar. 26, 1997, which claims benefit of U.S. Provisional Application Ser. No. 60/014,414, filed on Mar. 29, 1996.

FIELD OF THE INVENTION

This invention relates to a pharmaceutically active compound, a process for its production, compositions containing the compound and methods of using the compound in the treatment of certain disease states in mammals, in particular man. More specifically, the present invention relates to (E)-α-[2-n-butyl-1-[(4-carboxyphenyl)methyl]-1H-imidazol-5-yl]methylene-2-thiophenepropionic acid monomethanesulfonate dihydrate, a wet granulation process for preparing said compound, compositions containing this compound, and methods of using (E)-α-[2-n-butyl-1-[(4-carboxyphenyl)methyl]-1H-imidazol-5-yl]methylene-2-thiophenepropionic acid monomethanesulfonate dihydrate to block angiotensin II (AII) receptors and to treat hypertension, congestive heart failure and renal failure.

BACKGROUND OF THE INVENTION

The compound (E)-α-[2-n-butyl-1-[(4-carboxyphenyl) methyl]-1H-imidazol-5-yl]methylene-2-thiophenepropionic acid monomethanesulfonate is known by the name "eprosartan" and is the subject of U.S. Pat. No. 5,185,351 (the '351 patent), issued Feb. 9, 1993. This patent discloses in Example 41 a process for making the anhydrous form of (E)-α-[2-n-butyl-1-[(4-carboxyphenyl)methyl]-1H-imidazol-5-yl]methylene-2-thiophenepropionic acid monomethanesulfonate. Additionally, the '351 patent discloses conventional techniques for formulating (E)-α-[2-n-butyl-1-[(4-carboxyphenyl)methyl]-1H-imidazol-5-yl] methylene-2-thiophenepropionic acid monomethanesulfonate and Examples 108–111 specifically detail the preparation of certain formulations. This compound is claimed to have utility in blocking angiotensin II receptors and to be useful in the treatment of hypertension, congestive heart failure and renal failure.

Surprisingly, it has been found that the dihydrated form of (E)-α-[2-n-butyl-1-[(4-carboxyphenyl)methyl]-1H-imidazol-5-yl]methylene-2-thiophenepropionic acid monomethanesulfonate is formed in situ during the wet granulation process for preparing solid dosage forms of the anhydrous form of said compound. Additionally, it has been found that the dihydrate of eprosartan is obtained by recrysallizing the anhydrouus form from an aqueous acidic solution. The dihydrate has the improved property of being more compactible in the solid dosage form when compared to the corresponding anhydrous form of the compound. This is particularly important when formulating (E)-α-[2-n-butyl-1-[(4-carboxyphenyl)-methyl]-1H-imidazol-5-yl] methylene-2-thiophenepropionic acid monomethanesulfonate for therapeutic use.

SUMMARY OF THE INVENTION

The present invention provides a novel dihydrated form of (E)-α-[2-n-butyl-1-[(4-carboxyphenyl)methyl]-1H-imidazol-5-yl]methylene-2-thiophenepropionic acid monomethanesulfonate, in particular, in pharmaceutical compositions for the treatment of diseases in which blockade of angiotensin II receptors is indicated, for example, in the treatment of hypertension, congestive heart failure and renal failure.

The present invention also provides a process for preparing (E)-α-[2-n-butyl-1-[(4-carboxyphenyl)methyl]-1H-imidazol-5-yl]methylene-2-thiophenepropionic acid monomethanesulfonate dihydrate during wet granulation of the anhydrous form of (E)-α-[2-n-butyl-1-[(4-carboxyphenyl)methyl]-1H-imidazol-5-yl]methylene-2-thiophenepropionic acid monomethanesulfonate.

Another aspect of this invention provides a process for preparing (E)-α-[2-n-butyl-1-[(4-carboxyphenyl)methyl]-1H-imidazol-5-yl]methylene-2-thiophene-propionic acid monomethanesulfonate dibydrate by recrystallizing the anhydrous form of (E)-α[2-n-butyl-1-[(4-carboxyphenyl) methyl]-1H-imidazol-5-yl]methylene-2-thiophenepropionic acid monomethanesulfonate from an aqueous acidic solution, in particular, an aqueous solution of methanesulfonic acid.

Figure 1:
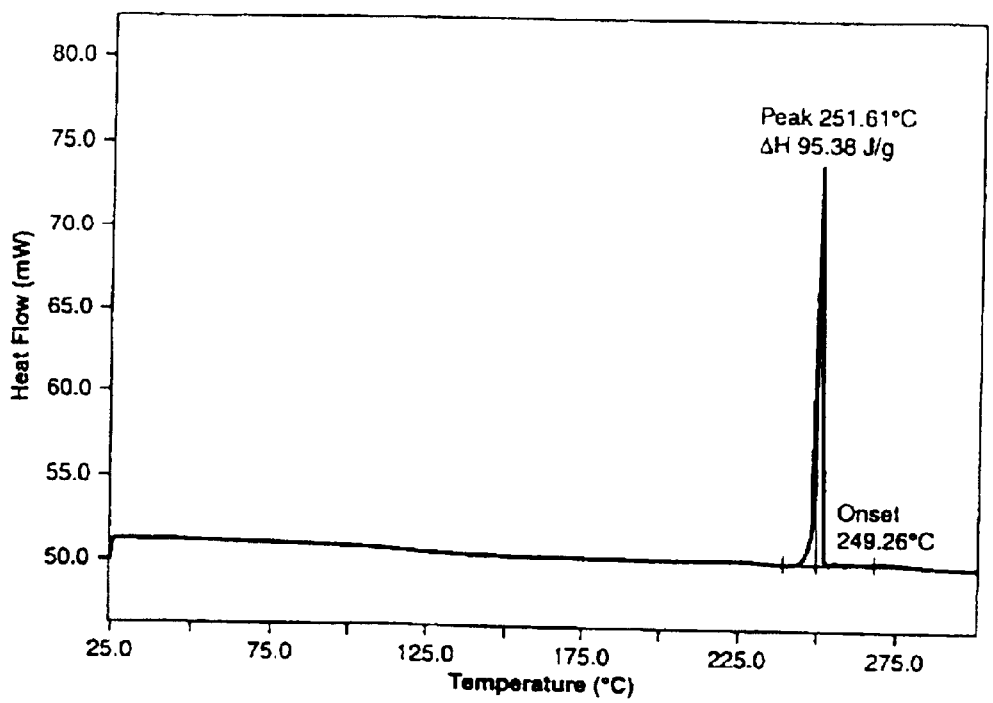
FIGS. 1, 3 and 5 show, respectively, the differential scanning calorimetric (DSC) thermogram, the thermogravimetric analysis (TGA) and the powder X-ray diffraction (XRD) pattern of the anhydrous form of (E)-α-[2-n-butyl-1-[(4-carboxyphenyl)methyl]-1H-imidazol-5-yl]methylene-2-thiophenepropionic acid monomethanesulfonate.

The anhydrous form of (E)-α-[2-n-butyl-1-[(4-carboxyphenyl)methyl]-1H-imidazol-5-yl]methylene-2-thiophenepropionic acid monomethanesulfonate exhibits a single thermal event, a melting endotherm at about 250° C. associated with a weight loss, suggesting that melting is followed by decomposition of the drug substance (FIG. 1). No significant weight loss prior to melting is observed in its TGA (thermnogravimetric analysis) [FIG. 3], suggesting that this compound does not contain significant quantities of surface adsorbed water and/or residual solvents. The powder X-ray diffraction pattern [FIG. 5] exhibits characteristic diffraction lines corresponding to 2θvalues of 7, 14, 18.9, 22.2 and 29 degrees.

Figure 2:
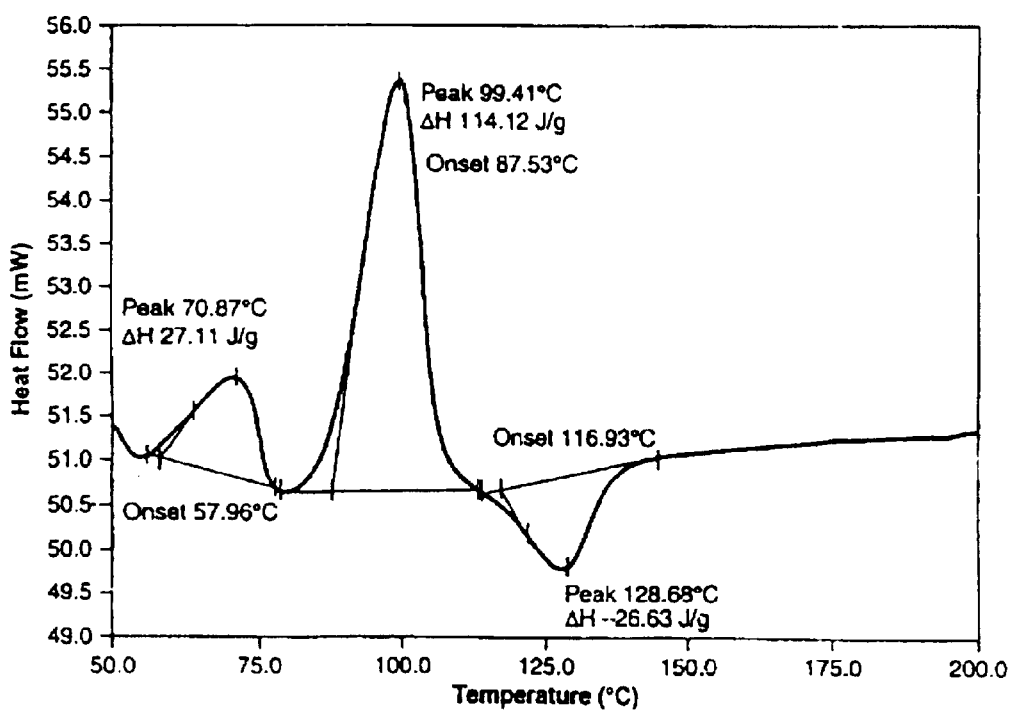
Figure 4:
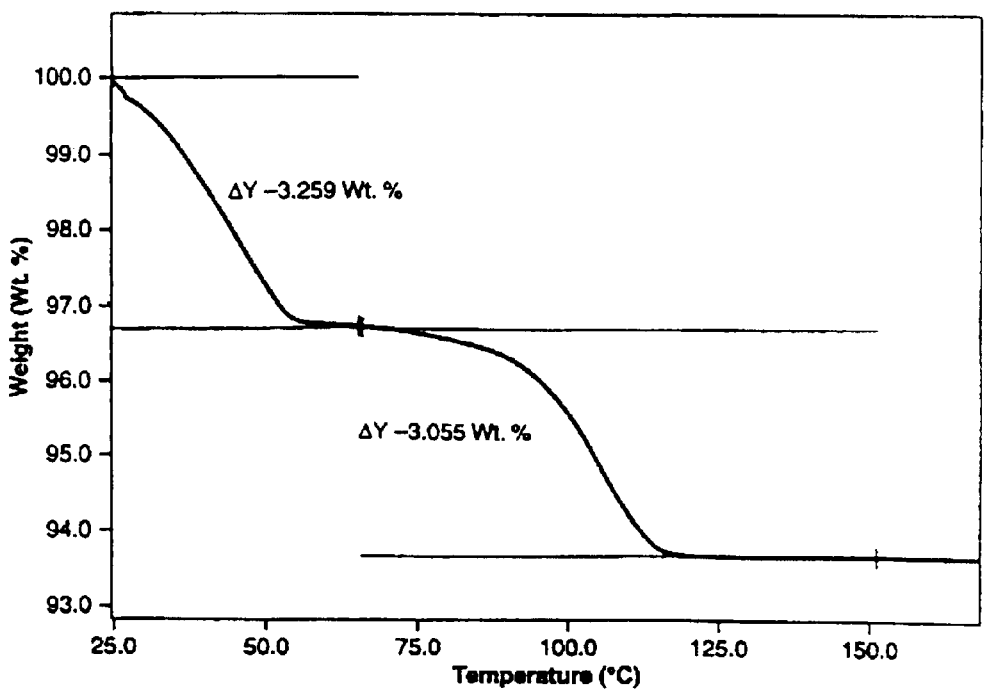
Figure 6:
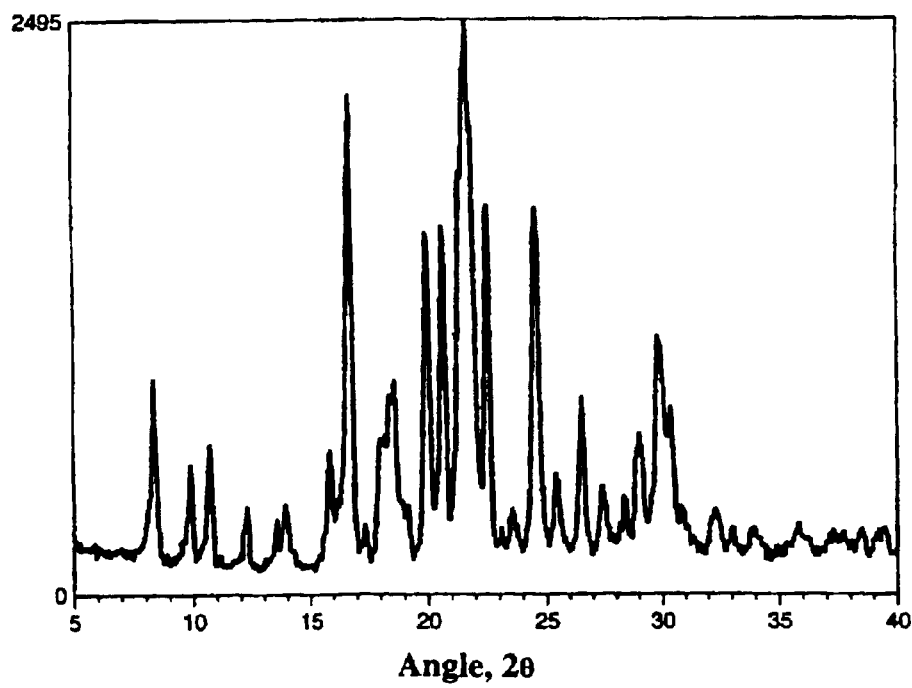

FIGS. 2, 4 and 6 show, respectively, the differential scanning calorimetric (DSC) thennogram, the thermogravimetric analysis (TGA) and the powder X-ray diffraction (XRD) pattern of the dihydrated form of (E)-α-[2-n-butyl-1-[(4-carboxyphenyl)methyl]-1H-imidazol-5-yl]methylene-2-thiophenepropionic acid monomethanesulfonate.

The DSC of the dihydrate [FIG. 2] exhibits 3 characteristic endothermic peaks at about 71° C., 99° C. and 250° C. The exotherm in FIG. 2 at 124° C. corresponds to the recrystallization of eprosartan dihydrate to the anhydrate upon dehydration. A typical TGA for the dihydrate obtained by granulating the anhydrous form of (E)-α-[2-n-butyl-1-[(4-carboxyphenyl)methyl]-1H-imidazol-5-yl]methylene-2-thiophenepropionic acid monomethanesulfonate with an excipient, such as lactose, xanthan gum, starch and gelatin, which act as a facilitator or stabilizer (i.e., stabilizing the dihydrate) exhibits a two-step moisture loss in the temperature range of 25–125° C. [FIG. 4]. The loss of water associated with the first-step moisture loss begins at 25° C. and is essentially complete by 70° C. This weight loss amounts to about 3%, corresponding stoichiometrically to one mole of water per mole of eprosartan anhydrate. The water associated with the second-step moisture loss is lost in the temperature range of 75–125° C. The dihydrate also exhibits a characteristic powder X-ray diffraction (XRD). The XRD [FIG. 6] exhibits characteristic diffraction lines corresponding to 2θvalues of 8, 10.8, 16.8, 21.9, 26.6 and 30.4 degrees.

Figure 3:
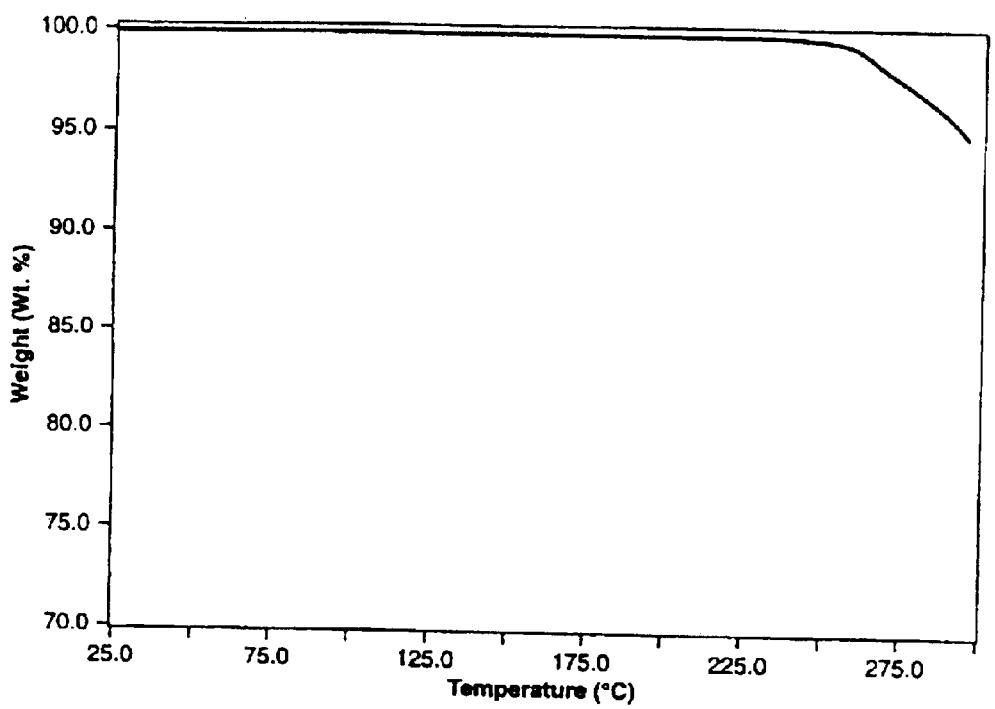
Figure 5:
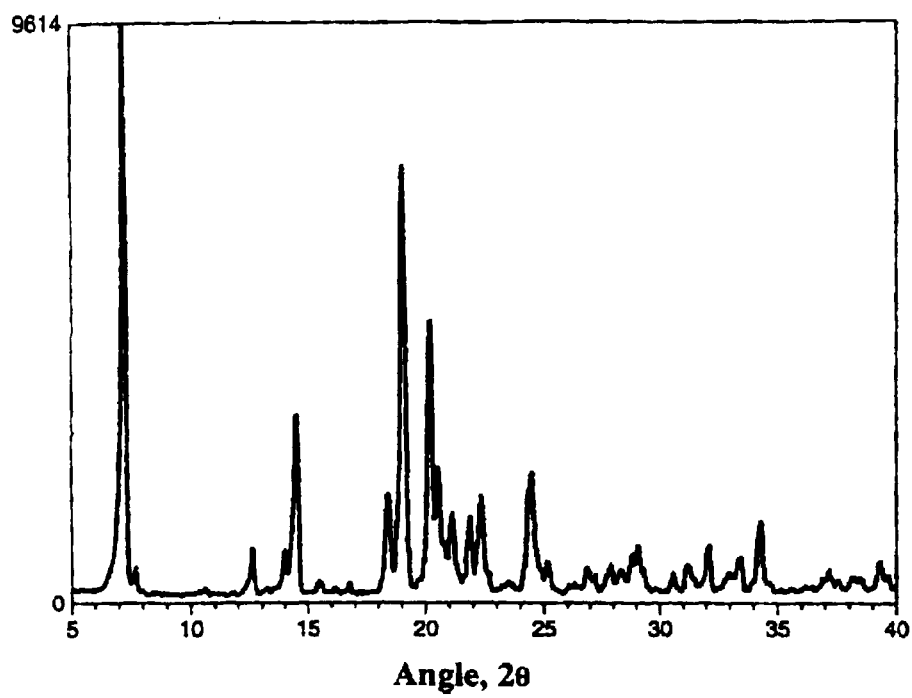

DETAILED DESCRIPTION OF THE INVENTION (E)-α-[2-n-Butyl-1-[(4-carboxyphenyl)methyl]-1H-imidazol-5-yl]methylene-2-thiophenepropionic acid monomethanesulfonate is known to exist in an anhydrous form and is characterized by the data shown in FIGS. 1, 3 and 5. This compound has the following structure:

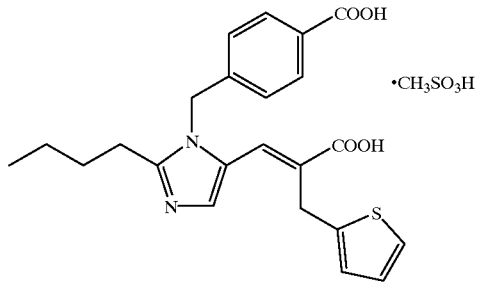

(E)-α-[2-n-Butyl-1-[(4-carboxyphenyl)methyl]-1H-imidazol-5-yl]methylene-2-thiophenepropionic acid monomethanesulfonate, eprosartan, is claimed in U.S. Pat. No. 5,185,351. Reference should be made to said patent for its full disclosure, including the methods of preparing and using this compound. The entire disclosure of the '351 patent is incorporated herein by reference.

Eprosartan is anhydrous, and, by itself, is stable at ambient temperature and humidity, as well as at accelerated conditions (30° C./79% RH or 40° C./75% RH for up to 6 months). This drug substance does not pick up moisture at higher humidities (typically up to 95% RH). However, the anhydrous form of the compound converts to the hydrated form, if it is moistened prior to storage in a closed container at ambient or higher temperatures, or if the dry powder is stored at a relative humidity of 98% or higher at ambient or higher temperatures for 8 days or longer. In the former case where the hydrate is obtained by moistening the drug substance, the hydrated form is not stable, and is generally converted back into the anhydrous form during drying.

In accordance with the present invention, it has been unexpectedly found that a stable dihydrated form of (E)-α-[2-n-butyl-1-[(4-carboxyphenyl)methyl]-1H-imidazol-5-yl] methylene-2-thiophenepropionic acid monomethane-sulfonate is produced in situ during the wet granulation processing of the anhydrous form of said compound into solid dosage forms (e.g., capsules and tablets). The granules containing (E)-α-[2-n-butyl-1-[(4-carboxyphenyl)methyl]-1H-imidazol-5-yl]methylene-2-thiophene-propionic acid monomethanesulfonate dihydrate are produced by mixing the anhydrous form of the compound with one or more pharmaceutically acceptable excipients, followed by granulation with water.

The dihydrated form of eprosartan can also be prepared by recrystallizing the anydrous form of eprosartan from an aqueous acidic solution, for example, an aqueous solution of methanesulfonic acid.

The dihydrate of the instant invention is characterized by the data shown in FIGS. 2, 4 and 6. The anhydrous form of (E)-α-[2-n-butyl-1-[(4-carboxyphenyl)-methyl]-1H-imidazol-5-yl]methylene-2-thiophene-propionic acid monomethane-sulfonate and its dihydrate have been characterized further. The crystal structure of both eprosartan anhydrate and eprosartan dihydrate have been determined from three-dimensional X-ray diffraction data collected on single crystals at ambient temperatures. The anhydrate crystallizes in the triclinic system, while the dihydrate crystallizes in the monoclinic system, with the following cell dimensions:

| Space Group and Unit cell Dimensions of Eprosartan | | |
|---|---|---|
| Parameter Space group | Anhydrate P1 | Dihydrate P2$_1$/C |
| a | 8.65A° | 18.35 A° |
| b | 12.68A° | 17.10 A° |
| c | 13.66A° | 17.35 A° |
| α | 112.7° | 90° |
| β | 101.4° | 90.8° |
| γ | 96.7° | 90° |

According to the instant invention, excipients, such as lactose, starch, poly(vinyl pyrrolidone) (Povidone, PVP), xanthan gum, sodium alginate and gelatin, in the granulation, added as a dry powder or in solution, facilitate the conversion of the anhydrate into the dihydrated form of (E)-α-[2-n-butyl-1-[(4-carboxyphenyl)-methyl]-1H-imidazol-5-yl]methylene-2-thiophenepropionic acid monomethane-sulfonate and they stabilize the dihydrate thus formed. Dihydrate formation is usually complete in about 2–10 minutes using a high shear wet granulation process in the preparation of solid dosage forms of (E)-α-[2-n-butyl-1-[(4-carboxyphenyl)-methyl]-1H-imidazol-5-yl]methylene-2-thiophene-propionic acid monomethane-sulfonate anhydrate. The granulation thus prepared, which contains the drug substance in the dihydrate form, can be dried, while keeping the drug substance in the hydrated form.

The process for preparing the solid dosage form containing the compound comprises: (i) producing granules containing (E)-α-[2-n-butyl-1-[(4-carboxy-phenyl)methyl]-1H-imidazol-5-yl]methylene-2-thiophene-propionic acid monomethanesulfonate in its dihydrated form in the presence of water and one or more pharmaceutically acceptable excipients and (ii) blending said granules with other pharmaceutically acceptable excipients to be filled into capsules or compressed into tablets exhibiting immediate release (100% release in a short period of time in a suitable dissolution medium) or modified release (sustained release or delayed release) profiles. This process for the preparation of solid dosage forms containing of (E)-α-[2-n-butyl-1-[(4-carboxyphenyl)methyl]-1H-imidazol-5-yl]methylene-2-thiophene-propionic acid monomethanesulfonate dihydrate comprises the in situ formation of a stable dihydrate of the compound during wet granulation, said formation being facilitated and stabilized by an excipient. Complete hydration takes place in about 2 minutes to 24 hours, preferably in about 2–10 minutes in the presence of preferred excipients.

In order to produce granules containing (E)-α-[2-n-butyl-1-[(4-carboxy-phenyl)methyl]-1H-imidazol-5-yl] methylene-2-thiophenepropionic acid in its dihydrated form, the anhydrous form of the compound is well mixed with pharmaceutically acceptable excipients, such as fillers, diluents, disintegrants and binders, granulated with water and dried to a predetermined water content (loss on drying).

Any combination of pharmaceutically acceptable excipients, e.g. diluents, fillers, binders and disintegrants, in desired proportions may be utilized in accordance with the wet granulation process of the present invention. The excipients commonly used in pharmaceutical industry are well described in the literature [refer to the Handbook of Pharmaceutical Excipients, A. Wade and P. J. Weller (Editors), American Pharmaceutical Association (1994)]. Pharmaceutically acceptable fillers and diluents include, but are not limited to, the following: lactose (hydrous as well as anhydrous), starch [unmodified (corn starch) or modified (for example, Starch 1500 available from Colorcon)], mannitol, sorbitol, cellulose, inorganic sulfates and phosphates. Disintegrants include, but are not limited to, the following: sodium starch glycolate, sodium carmellose and crosslinked polyvinyl pyrrolidone, and binders include, but are not limited to, the following: gelatin, corn starch, modified starch (Starch 1551, pregelatinized starch), hydroxypropyl methyl cellulose (HPMC) and hydroxypropyl cellulose (HPC). Examples of excipients suitable for modified release applications include, but are not limited to, the following: high molecular weight HPMCs, polymethacrylate polymers known as Eudragits, polyethylene oxide, Polyox® (Union Carbide Corporation), modified ethyl cellulose, Surelease® (Colorcon), crosslinked acrylic acid polymers, Carbopol® (BF Goodrich Speciality Chemicals) and waxy materials, such as glyceryl behenate (Compritol®), glyceryl palrmitostearate (Precirol®), and Gelucires® [all from Gattefosse S.a., France] and carnauba wax.

Preferably, the pharmaceutically acceptable excipients used as binders, diluents and fillers during the wet granulation process of this invention are lactose, starch (corn starch, soluble starch, or Starch 1551), gelatin, xanthan gum, sodium alginate, Povidone (PVP), and microcrystalline or powdered cellulose, each one of which acts as a facilitator in the formation of a stable dihydrate of eprosartan. More preferably, the excipients are lactose, Starch 1551, cellulose, and Povidone (PVP). Most preferably, the excipients are lactose, cellulose and Starch 1551.

Preferably, the excipients used in the wet granulation process are present in 1–70% on a weight for weight basis depending on the unit dose strength of eprosartan required. Most preferably, the excipients may be present at as low as 1–7% on a weight for weight basis in order to produce granulations with a high drug load.

The process for preparing the solid dosage forms in accordance with the present invention may be carried out using a planetary mixture, a V-blender, a high shear granulator, a fluid bed granulator or a tableting machine. Optionally, the anhydrous form of (E)-α-[2-n-butyl-1-[(4-carboxyphenyl)methyl]-1H-imidazol-5-yl]methylene-2-thiophenepropionic acid monomethanesulfonate may be granulated first with a suitable excipient using a conventional granulating equipment, said excipient stabilizing the dihydrate which is formed in about 2–10 minutes (time duration for a high shear granulation). Optionally, drying of the granulation may be avoided by using less water at the granulation stage, and the granulation thus produced is suitable for the preparation of direct compression immediate or modified release dosage forms. Optionally, the immediate release tablet cores may be coated with a membrane of a polymer imparting delayed or sustained release properties.

Thus, the present invention provides a pharmaceutical composition which comprises (E)-α-[2-n-butyl-1-[(4-carboxyphenyl)methyl]-1H-imidazol-5-yl]methylene-2-thiophenepropionic acid monomethanesulfonate dihydrate and a pharmaceutically acceptable carrier. The pharmaceutical composition is adapted for oral administration. The composition is presented as a unit dose pharmaceutical composition containing from about 50 mg to about 1.0 g of (E)-α-[2-n-butyl-1-[(4-carboxyphenyl)methyl]-1H-imidazol-5-yl]methylene-2-thiophenepropionic acid monomethanesulfonate dihydrate, preferably from about 200 to about 400 mg. Such a composition is normally taken from 1 to 4 times daily, preferably from 1 to 2 times daily. The preferred unit dosage forms include tablets or capsules. The compositions of this invention may be formulated by conventional methods of admixture such as blending, filling and compressing. Suitable pharmaceutically acceptable carriers for use in this invention include diluents, fillers, binders and disintegrants.

(E)-α-[2-n-Butyl-1-[(4-carboxyphenyl)methyl]-1H-imidazol-5-yl]methylene-2-thiophenepropionic acid monomethanesulfonate dihydrate may be co-administered with other pharmaceutically active compounds, for example, in physical combination or by sequential administration. Conveniently, the compound of this invention and the other active compound are formulated in a pharmaceutical composition. Thus, this invention also relates to pharmaceutical compositions comprising (E)-α-[2-n-butyl-1-[(4-carboxyphenyl)methyl]-1H-imidazol-5-yl]methylene-2-thiophenepropionic acid monomethanesulfonate dihydrate, a pharmaceutically acceptable carrier, and a second pharmaceutically active compound selected from the group consisting of a diuretic, a calcium channel blocker, a β-adrenoceptor blocker, a renin inhibitor, and an angiotensin converting enzyme inhibitor. Examples of compounds which may be included in pharmaceutical compositions in combination with (E)-α-[2-n-butyl-1-[(4-carboxyphenyl)methyl]-1H-imidazol-5-yl]methylene-2-thiophenepropionic acid monomethanesulfonate dihydrate are diuretics, particularly a thiazide diuretic, such as hydrochlorothiazide, or a loop diuretic, such as furosemide, calcium channel blockers, particularly dihydropyridine antagonists, such as nifedipine, β-adrenoceptor blockers, such as propranolol, renin inhibitors, such as enalkinen, and angiotensin converting enzyme inhibitors, such as captopril or enalapril. Preferably, the pharmaceutical composition contains 200–400 mg of (E)-α-[2-n-butyl-1-[(4-carboxyphenyl)-methyl]-1H-imidazol-5-yl]methylene-2-thiophene-propionic acid monomethanesulfonate dihydrate in combination with 6.25–25 mg of hydrochlorothiazide.

No unacceptable toxicological effects are expected when (E)-α-[2-n-butyl-1-[(4-carboxyphenyl)methyl]-1H-imidazol-5-yl]methylene-2-thiophenepropionic acid monomethanesulfonate dihydrate is administered in accordance with the present invention.

(E)-α-[2-n-Butyl-1-[(4-carboxyphenyl)methyl]-1H-imidazol-5-yl]methylene-2-thiophenepropionic acid monomethanesulfonate dihydrate is useful for treating diseases in which blockade of the angiotensin II receptor would be beneficial. Preferably, this compound is used alone or in combination with said second pharmaceutically active compounds in the treatment of hypertension, congestive heart failure and renal failure. Additionally, (E)-α-[2-n-butyl-1-[(4-carboxy-phenyl)methyl]-1H-imidazol-5-yl]methylene-2-thiophenepropionic acid monomethanesulfonate dihydrate is of value in the treatment of left ventricular hypertrophy regression, diabetic nephropathy, diabetic retinopathy, mascular degeneration, haemorrhagic stroke, primary and secondary prevention of infarction, prevention of atheroma progression and the regression of atheroma, prevention of restinosis after angioplasty or bypass surgery, improving cognitive function, angina, glaucoma, and CNS disorders, such as anxiety.

The following examples are illustrative of the instant invention. These examples are not intended to limit the scope of this invention as defined hereinabove and as claimed hereinbelow.

In Examples 1–5, below, the term "internals" means the ingredients which are granulated and the term "externals" means the ingredients which are blended with the granulation.

EXAMPLES

Examples 1–5

Preparation and Formulation of (E)-α-[2-n-Butyl-1-[(4-carboxyphenyl)methyl]-1H-imidazol-5-yl]methylene-2-thiophenepropionic Acid Monomethanesulfonate Dihydrate

TABLE I

Formulation Summary

|  | Example 1 (%) | Example 2 (%) | Example 3 (%) | Example 4 (%) | Example 5 (%) |
|---|---|---|---|---|---|
| Internals |  |  |  |  |  |
| Compound A * | 30–50 | 60–80 | 50–70 | 50–70 | 50–70 |
| Lactose, hydrous | 15–30 | 7–20 | 1–5 | 2–7 | 1–4 |
| Cellulose (Avicel) | 2–15 | 7–20 | — | 2–8 | — |
| Starch 1551 | 2–7 | — | — | 2–9 | — |
| Povidone (PVP) | — | 2–8 | — | — | — |
| Purified water | ** | ** | ** | ** | ** |
| Externals |  |  |  |  |  |
| Polyethylene oxide | — | — | 5–25 | — | — |
| Glyceryl behenate |  |  |  |  | 5–25 |
| Avicel PH102 | 10–20 | 5–25 | 5–25 | 10–25 | 5–25 |
| Corn starch | 3–7 | — | — | — | — |
| Ac-Di-Sol | — | 2–8 | — | 2–8 | — |
| Mag. stearate | 0.5–1.5 | 0.5–1.5 | 0.2–1.0 | 0.5–1.5 | 0.2–1.0 |

* (E)-α-[2-n-butyl-1-[(4-carboxyphenyl)methyl]-1H-imidazol-5-yl]methylene-2-thiophenepropionic acid monomethanesulfonate, anhydrous form
** Composition does not take into account the formation of the dihydrate during granulation.

Table I, above, summarizes the amounts of Compound A and excipients on a weight for weight basis used in the formulations detailed in Examples 1–5 below.

Example 1

A fluid bed granulator, UniGlatt, is charged with the anhydrous form of (E)-α-[2-n-butyl-1-[(4-carboxyphenyl)methyl]-1H-imidazol-5-yl]methylene-2-thiophenepropionic acid monomethanesulfonate and Impalpable Lactose, homogenized with an aqueous suspension of Starch 1551 and granulated by spraying at a desirable flow rate and dry wet mass to an LOD (loss on drying) of 5.5–6.5% determined using a Sartorius moisture meter tested at 110° C. The hydrate formation is checked by TGA and powder X-ray diffraction. The dry granulation is processed through a #30 mesh screen and then a compression mix is prepared by blending with the externals and the tablets are manufactured.

Example 2

The internals are premixed in the Collette bowl for 1 min at a low chopper setting and granulated for 4 min by adding water (added in parts) at a high chopper setting. The granulate is then milled through an appropriate screen and dried to an LOD of 5.5–6.5%. The dried granulate is milled, mixed with the externals and compressed into tablets. The tablets have been shown to contain the drug substance in the dihydrate form.

Example 3

The internals are premixed in a high shear granulator and granulated at a high chopper setting with hydrous lactose added in solution. The granulate, containing the active in the dihydrated form, is mixed with the externals [polyethylene oxide of high molecular weight (Polyox®, Union Carbide Corporation), microcrystalline cellulose (Avicel PH102), and magnesium stearate] and compressed into tablets which exhibit sustained release profiles.

Example 4

A scaled up batch is manufactured using a 700 liter high shear Fielder granulator, Quadro Comnil fitted with ¼" screen for wet milling and a #20 mesh screen for dry milling, a fluid bed dryer for a total moisture content (LOD) of about 6% and a Manesty Unipress for compressing tablets of hardness in the range of 8–20 kP. The tablets thus manufactured have been shown to contain the active ingredient in the dihydrated form.

Example 5

A granulation (batchsize: 8 kgs) of (E)-α-[2-n-butyl-1-[(4-carboxyphenyl)-methyl]-1H-imidazol-5-yl]methylene-2-thiophenepropionic acid monomethanesulfonate dihydrate is manufactured in a 25 liter Fielder bowl using a solution of lactose at a high chopper setting. The granulation mixed with glyceryl behenate [Compritol®, Gattefosse S.a.] is roller compacted, milled and sifted. #18–40 mesh cut granules are subjected to a thermal treatment using a bed granulator at about 65° C. for 15 min. The cooled granulate, containing the active in the dihydrated form, is mixed with the externals and compressed into tablets exhibiting sustained release profiles.

Example 6

Preparation of (E)-α-[2-n-Butyl-1-[(4-carboxyphenyl)methyl]-1H-imidazol-5-yl]methylene-2-thiophenepropionic Acid Monomethanesulfonate Dihydrate Eprosartan anhydrate was suspended in an aqueous solution of 3.0 M methanesulfonic acid. The suspension was continuously stirred and heated to 65–70° C. The filtrate obtained by suction was maintained at 75° C. for several minutes to ensure the absence of the anhydrate in solution. The solution was slowly cooled to ambient temperature and clear colorless crystalline drug substance was harvested by filtration and air dried.

It is to be understood that the invention is not limited to the embodiments illustrated hereinabove and the right is reserved to the illustrated embodiments and all modifications coming within the scope of the following claims.

What is claimed is:

1. A compound which is (E)-α-[2-n-butyl-1-[(4-carboxyphenyl)methyl]-1H-imidazol-5-yl]methylene-2-thiophenepropionic acid monomethanesulfonate dihydrate.

2. A process for the preparation of the compound according to claim 1 which comprises recrystallizing the anhydrous form of (E)-α-[2-n-butyl-1-[(4-carboxyphenyl)methyl]-1H-imidazol-5-yl]methylene-2-thiophenepropionic acid monomethanesulfonate from an aqueous solution containing an acid.

3. The process according to claim 2 wherein the acid is methanesulfonic acid.

4. A process for the preparation of the compound according to claim 1 which comprises:
   (i) mixing the anhydrous form of (E)-α-[2-n-butyl-1-[(4-carboxy-phenyl)methyl]-1H-imidazol-5-yl]methylene-2-thiophenepropionic acid monomethanesulfonate with one or more pharmaceutically acceptable excipients;
   (ii) granulating the mixture with water; and
   (iii) drying the granulation to a predetermined water content.

5. The process according to claim 4 wherein the pharmaceutically acceptable excipient is selected from the group consisting of diluents, fillers, binders, disintegrants and lubricants.

6. A pharmaceutical composition comprising the compound according to claim 1 and a pharmaceutically acceptable carrier.

7. A process for the preparation of a solid dosage form containing the compound according to claim 1 which comprises:
   (i) producing granules containing (E)-α-[2-n-butyl-1-[(4-carboxy-phenyl)methyl]-1H-imidazol-5-yl]methylene-2-thiophenepropionic acid monomethanesulfonate dihydrate; and
   (ii) blending said granules with other pharmaceutically acceptable excipients to be filled into a capsule or compressed into a tablet.

8. A process for the preparation of a solid dosage form containing the compound according to claim 1 which comprises:
   (i) storing the anhydrous form of (E)-α-[2-n-butyl-1-[(4-carboxyphenyl)methyl]-1H-imidazol-5-yl]methylene-2-thiophenepropionic acid monomethanesulfonate at a relative humidity of 98% or higher at ambient or high temperatures for 8 days or longer;
   (ii) producing granules containing the dihydrate and (iii) blending said granules with other pharmaceutically acceptable excipients to be filled into a capsule or compressed into a tablet.

9. A process for the preparation of a solid dosage form containing the compound according to claim 1 which comprises:
   (i) recrystallizing the anhydrous form of (E)-α-[2-n-butyl-1-[(4-carboxy-phenyl)methyl]-1H-imidazol-5-yl] methylene-2-thiophenepropionic acid monomethanesulfonate from an aqueous solution containing an acid;
   (ii) producing granules containing the dihydrate and
   (iii) blending said granules with other pharmaceutically acceptable excipients to be filled into a capsule or compressed into a tablet.

10. The process according to claim 9 wherein the acid is methanesulfonic acid.

11. A pharmaceutical composition comprising the compound according to claim 1, a pharmaceutically acceptable carrier and a second pharmaceutically active compound selected from the group consisting of a diuretic, a calcium channel blocker, a β-adrenoceptor blocker, a renin inhibitor, and an angiotensin converting enzyme inhibitor.

12. The pharmaceutical composition according to claim 11 wherein the second pharmaceutically active compound is a diuretic.

13. The pharmaceutical composition according to claim 12 wherein the diuretic is hydrochlorothiazide.

14. The pharmaceutical composition according to claim 11 wherein the second pharmaceutically active compound is a loop diuretic.

15. The pharmaceutical composition according to claim 14 wherein the loop diuretic is furosemide.

16. The pharmaceutical composition according to claim 11 wherein the second pharmaceutically active compound is a calcium channel blocker.

17. The pharmaceutical composition according to claim 16 wherein the calcium channel blocker is nifedipine.

18. The pharmaceutical composition according to claim 11 wherein the second pharmaceutically active compound is a β-adrenoceptor blocker.

19. The pharmaceutical composition according to claim 18 wherein the β-adrenoceptor blocker is propranolol.

20. The pharmaceutical composition according to claim 11 wherein the second pharmaceutically active compound is an angiotensin converting enzyme inhibitor.

21. The pharmaceutical composition according to claim 18 wherein the angiotensin converting enzyme inhibitor is captopril or enalapril.

22. The pharmaceutical composition according to claim 11 wherein the second pharmaceutically active compound is a renin inhibitor.

23. The pharmaceutical composition according to claim 20 wherein the renin inhibitor is enalkinen.

24. A method of blocking angiotensin II receptors which comprises administering to a subject in need thereof an effective amount of the compound according to claim 1.

25. A method of treating hypertension which comprises administering to a subject in need thereof an effective amount of the compound according to claim 1.

26. A method of treating hypertension which comprises administering stepwise or in physical combination the compound according to claim 1 and a second pharmaceutically active compound selected from the group consisting of a diuretic, a calcium channel blocker, a β-adrenoceptor blocker, a renin inhibitor, and an angiotensin converting enzyme inhibitor.

27. The method according to claim 26 wherein the second pharmaceutically active compound is a diuretic.

28. The method according to claim 27 wherein the diuretic is hydrochlorothiazide.

29. The method according to claim 26 wherein the second pharmaceutically active compound is a loop diuretic.

30. The method of claim 29 wherein the loop diuretic is furosemide.

31. The method according to claim 26 wherein the second pharmaceutically active compound is a calcium channel blocker.

32. The method according to claim 31 wherein the calcium channel blocker is nifedipine.

33. The method according to claim 26 wherein the second pharmaceutically active compound is a β-adrenoceptor blocker.

34. The method according to claim 33 wherein the β-adrenoceptor blocker is propranolol.

35. The method according to claim 26 wherein the second pharmaceutically active compound is an angiotensin converting enzyme inhibitor.

36. The method according to claim 35 wherein the angiotensin converting enzyme inhibitor is captopril or enalapril.

37. The method according to claim 26 wherein the second pharmaceutically active compound is a renin inhibitor.

38. The method according to claim 37 wherein the renin inhibitor is enalkinen.

39. A method of treating congestive heart failure which comprises administering to a subject in need thereof an effective amount of the compound according to claim 1.

40. A method of treating renal failure which comprises administering to a subject in need thereof an effective amount of the compound according to claim 1.

41. A compound according to claim 1 for use as a medicament.

* * * * *